United States Patent [19]
Fabrizi et al.

[11] Patent Number: 5,300,427
[45] Date of Patent: Apr. 5, 1994

[54] BUFFER SOLUTIONS CONTAINING COLLAGENASE, THEIR PREPARATION AND USE FOR DILUTING HUMAN SERA

[75] Inventors: Paolo Fabrizi, Monteriggioni; Francesco Donnini, Arezzo, both of Italy

[73] Assignee: Sclavo S.p.A., Siena, Italy

[21] Appl. No.: 713,072

[22] Filed: Jun. 11, 1991

[30] Foreign Application Priority Data

Jun. 13, 1990 [IT] Italy ................ 20630A/90

[51] Int. Cl.$^5$ .................. C12Q 1/37; C12Q 1/34; C12N 9/50
[52] U.S. Cl. ........................ 435/7.92; 435/219; 435/7.1; 435/18
[58] Field of Search ............ 435/7.92, 7.9, 7.1, 435/7.2, 219, 18; 530/387; 424/409, 94.3, 94.67, 94.63; 436/18

[56] References Cited

U.S. PATENT DOCUMENTS

| | | | |
|---|---|---|---|
| 4,816,400 | 3/1989 | Tryggvason et al. | 435/219 X |
| 4,931,385 | 6/1990 | Block et al. | 435/7.94 |
| 4,944,941 | 7/1990 | Ammann | 424/85.5 |
| 4,985,542 | 1/1991 | Fillit et al. | 530/395 |

OTHER PUBLICATIONS

Wang et al. (1988) *J. Parenteral Sci, Technol.*, 42, (2S), S1–S26.

*Primary Examiner*—Douglas W. Robinson
*Assistant Examiner*—Jon P. Weber
*Attorney, Agent, or Firm*—Birch, Stewart, Kolasch & Birch

[57] ABSTRACT

A human sera dilution buffer solution containing the enzyme collagenase is described, for use in preventing false positive indication reactions taking place when specific IgMs are sought in human sera by ELISA capture assays, in which the enzymatic conjugate consists of antibodies bound to ALP with glutaraldehyde.

5 Claims, No Drawings

BUFFER SOLUTIONS CONTAINING COLLAGENASE, THEIR PREPARATION AND USE FOR DILUTING HUMAN SERA

FIELD OF THE INVENTION

The present invention relates to a buffer solution of pH 7.0–7.5 containing collagenase, and its use in ELISA capture methods for detecting class specific antibodies, these methods being based on the use of enzymatic conjugates in which the enzyme is bound to the antibody by glutaraldehyde.

STATE OF THE ART

It is known that the C1q complement factor present in human serum possesses six claviform filaments representing the recognition elements for particular sites present on IgGs and IgMs (Shelton E. et al., Proc. Natl. Acad. Sci. USA, 1972, 69:65). The affinity of C1q is lower for monomer IgGs than for IgMs and aggregate antibodies (IgG and IgM) either bound to the antigen or denatured (Sledge C.R. and Bing D.H., J. Biol. Chem. 1973, 248:2818).

The present inventors theorize that the presence of macromolecular complexes consisting of C1q and IgM antibodies in the serum is responsible for false positive results in detecting specific IgMs by the ELISA antibody capture assay using detector antibodies conjugated with alkaline phosphatase (ALP) by glutaraldehyde, and that this theory is generally applicable to all ELISA assays based on the capture of class specific antibodies.

By bringing the serum into contact with the solid phase, represented by microplate walls coated with anti-human IgM antibodies, these IgM-C1q complexes are captured. Subsequently, adding the antibody conjugated with ALP, previously combined with the antigens towards which the IgMs are sought, to the well this binds to the Cq1 and when brought into contact with a substrate specific for ALP, generates an aspecific signal.

In contrast, when the buffer solution of the present invention is used to dilute the sera, the collagenase enzyme contained in it acts on the amino acid sequences of the C1q to separate it from those filaments able to bind the IgMs.

DETAILED DESCRIPTION OF THE INVENTION

The buffer solution according to the invention consists of:

| | |
|---|---|
| Anhydrous sodium biphosphate: | 1.09 g/l |
| Sodium monophosphate monohydrate: | 0.37 g/l |
| Sodium chloride: | 8.5 g/l |
| Bovine albumen serum: | 10 g/l |
| Brij-35: | 0.5 g/l |
| Human IgG aggregates: | 0.5 g/l |
| Collagenase type IV: | 1000-3000 U/l |
| Sodium azide: | 1.00 g/l | and has a pH of 7.0–7.5.

METHOD OF PREPARING THE BUFFER SOLUTION 1.09 g of anhydrous sodium bisulphate, 0.37 g of sodium monophosphate monohydrate and 8.5 g of sodium chloride are dissolved in 900 ml of sterile distilled water. This solution is then adjusted to pH 7.2 with 0.1N sodium hydroxide and 10.0 g of bovine albumen serum are then added to it and dissolved by slowly stirring for about 30 minutes. The following reagents are then added to the solution subsequently obtained:

| | |
|---|---|
| Brij-35: | 0.50 g |
| Human IgG aggregates: | 0.50 l |
| Collagenase type IV: | 1500.00 U/l |
| Sodium azide: | 1.00 g |

On termination, after adjusting the final volume to 1000 ml with sterile distilled water, the solution is filtered under sterile conditions through filter membranes. The vessels necessary for preparing and storing the solution must have been previously sterilized.

Some examples are given to better illustrate the objects and advantages of the present invention, but without imposing any limit thereon.

EXAMPLE 1

ELISA on a panel of false positive sera to compare a sera-diluent buffer solution as such with one to which collagenase has been added.

About 100 serum samples pertaining to a mixed population (blood donors and pregnant women) which had proved negative by an IFA reference method were assayed by an IgM capturing ELISA based on a detection system consisting of antibodies conjugated with ALP and precombined with extractive antigens of various micro-organisms (Toxoplasma gondii, Rubella virus, Cytomegalovirus and Treponema pallidum). The assay gave the following results: 94 negative sera and 6 false positive sera.

Aliquots of all six false positive sera were diluted with the diluent buffer solution both as such (anhydrous sodium biphosphate 1.09 g/l, sodium monophosphate monohydrate 0.37 g/l, sodium chloride 8.5 g/l, bovine albumen serum 10 g/l, Brij-35 0.5 g/l, aggregate human IgG 0.5 g/l, sodium azide 1.00 g/l), and to which collagenase had been added at a concentration of 0.01 g/l, equivalent to an enzymatic activity of 1500 I.U., and were assayed in duplicate by the IgM capture ELISAs previously used for their selection, these assays comprising the following stages:

Stage 1:

The well walls of microtitre plates (Nunc-MBC Denmark) were saturated by physical absorption, by incubating 0.100 ml/well of a 20 µg/ml solution of anti-human IgM antibodies (µ chain) in 0.1M $Na_2CO_3$ buffer solution at pH 9.8 overnight at ambient temperature (20°–25° C.) in a moist chamber.

Stage 2

After three washes with distilled water containing 0.05% of Tween 20, 0.100 ml/well of the negative and positive control sera and of the sera under examination diluted 1:101 in physiological solution buffered at pH 7.2 containing 0.05% Brij-35 and 0.1% bovine albumen (BSA) were added to the plates.

Collagenase (type IV, specific activity 150 U/mg, Worthington) concentration 1.5 U/ml was added in some experiments to the aforesaid sera-diluent buffer solution. The plates were incubated for one hour at 37° C.

Stage 3

After five washes with buffered physiological solution containing 0.05% Brij-35, 0.100 ml/well of a complex consisting of antibodies conjugated with ALP (Ab-ALP) combined with extractive antigens (Ag) of Toxoplasma gondii (Toxo), of Rubella virus (Rubella), of Lytomeglovirus (CMV) or of Treponema pallidum (Sifilide) in optimum dilutions (Ag: 10-20 μg/ml; Ab-ALP: 5-10 μg/ml) in buffered physiological solution containing 0.05% Brij-35 and 0.1% BSA were added to the plates.

The plates were incubated for 1 hour at 37° C.

Stage 4

After five washes with buffered physiological solution containing 0.05% Brij-35, 0.100 ml/well of a solution of 1 mg/ml of p-nitrophenyl-phosphate (AlP specific chromogenic substrate) in 1.1M diethanolamine buffer solution at pH 9.8 containing 0.6 mM $MgCl_2$ were added to the plates. The plates were incubated for exactly 30 minutes at 37° C., after which 0.025 ml/well of 3M NaOH was added to block the enzymatic reaction.

The absorbance of the solutions in the wells was determined with a microplate photometer with vertical reading at 405 nm after zeroing against air.

The absorbance threshold value for discriminating negative from positive (cut-off) was calculated by the following formula:

Cut-off=(Mean absorbance negative control+mean absorbance positive control)×0.5

Those sera showing an absorbance less than the cut-off value were considered negative and those showing an absorbance greater than or equal to this value were considered positive.

The results obtained are shown in Table 1 and show that the addition of collagenase (1.5 U/ml) to the sera-diluent buffer solution shows all the false positive sera as negative (mean absorbance<cut-off value).

EXAMPLE 2

ELISA: comparison between sera-diluent buffer solution as such and with collagenase added, assaying a positive sera panel.

Twenty sera, divided into four groups of five sera which had proved respectively positive in IgM anti Toxoplasma gondii, anti Rubella virus, anti CMV and anti Treponema pallidum using a reference method (IFA), were diluted with diluent buffer solution both as such (anhydrous sodium biphosphate 1.09 g/l, sodium monophosphate monohydrate 0.37 g/l, sodium chloride 8.5 g/l, bovine albumen serum 10 g/l, Brij-35 0.5 g/l, aggregate human IgG 0.5 g/l, sodium azide 1.00 g/l), and to which type IV collagenase had been added (1500 U/l). They were then analyzed using the ELISA assays described in Example 1. The results obtained are shown in Table 2 and demonstrate that the addition of collagenase to the sera-diluent buffer solution do not cause any absorbance changes in the true positive sera which are significant from the diagnostic aspect.

TABLE 1

| False positive serum Buffer: | Mean absorbance at 405 nm | | | | | | | |
|---|---|---|---|---|---|---|---|---|
| | Assay A | | Assay B | | Assay C | | Assay D | |
| | 1 | 2 | 1 | 2 | 1 | 2 | 1 | 2 |
| 1 | 0.935 | 0.215 | 0.897 | 0.285 | 0.972 | 0.221 | 1.522 | 0.221 |
| 2 | 1.120 | 0.310 | 0.902 | 0.195 | 0.853 | 0.157 | 1.638 | 0.157 |
| 3 | 1.015 | 0.225 | 0.956 | 0.236 | 0.910 | 0.256 | 1.305 | 0.219 |
| 4 | 1.453 | 0.289 | 1.237 | 0.272 | 0.790 | 0.192 | 1.602 | 0.256 |
| 5 | 0.872 | 0.238 | 0.872 | 0.244 | 0.656 | 0.273 | 0.907 | 0.192 |
| 6 | 0.649 | 0.201 | 0.854 | 0.176 | 0.567 | 0.220 | 0.853 | 0.273 |
| Cut-off | 0.536 | 0.545 | 0.392 | 0.295 | 0.493 | 0.463 | 0.377 | 0.306 |

Buffer 1: buffered physiological + Brig-35 (0.05%) + BSA (0.1%);
Buffer 2: buffer 1 + collagenase (1.5 U/ml)
Assay A: ELISA Toxo IgM; Assay B: ELISA Rubella IgM;
Assay C: ELISA CMVIgM; Assay D: ELISA Sifilide IgM

TABLE 2

| True positive serum Buffer: | Mean absorbance at 405 nm | | | | | | | |
|---|---|---|---|---|---|---|---|---|
| | Assay A | | Assay B | | Assay C | | Assay D | |
| | 1 | 2 | 1 | 2 | 1 | 2 | 1 | 2 |
| 1 | 1.258 | 1.210 | 0.990 | 0.985 | 0.913 | 0.857 | 0.730 | 0.756 |
| 2 | 0.901 | 0.820 | 1.935 | 1.787 | 1.267 | 1.218 | 1.310 | 1.230 |
| 3 | 0.887 | 0.915 | 1.130 | 1.102 | 0.723 | 0.738 | 0.907 | 0.835 |
| 4 | 1.510 | 1.457 | 0.680 | 0.673 | 0.972 | 0.948 | 1.122 | 0.972 |
| 5 | 0.737 | 0.697 | 1.352 | 1.321 | 1.570 | 1.451 | 1.478 | 1.528 |
| Cut-off | 0.550 | 0.525 | 0.405 | 0.365 | 0.485 | 0.496 | 0.345 | 0.330 |

Buffer 1: buffered physiological + Brig-35 (0.05%) + BSA (0.1%);
Buffer 2: buffer 1 + collagenase (1.5 U/ml)
Assay A: ELISA Toxo IgM; Assay B: ELISA Rubella IgM;
Assay C: ELISA CMVIgM; Assay D: ELISA Sifilide IgM.

We claim:

1. A pH 7.0-7.5 phosphate buffer solution for diluting human sera for immunoassays containing type IV collagenase in a concentration of 1000-3000 U/l, sodium chloride, bovine serum albumin, Brij-35, aggregate human IgG and sodium azide.

2. A buffer solution as claimed in claim 1, wherein said collagenase is present in a concentration of 1500 U/l.

3. A buffer solution as claimed in claim 1, consisting of: anhydrous sodium biphosphate 1.09 g/l, sodium monophosphate monohydrate 0.37 g/l, sodium chloride 8.5 g/l, bovine albumen serum 10 g/l, Brij-35 0.5 g/l, aggregate human IgG 0.5 g/l, type IV collagenase 1500 U/l., sodium azide 1.00 g/l.

4. A buffer solution as claimed in claim 1 wherein the collagenase is present in a concentration of 1000 U/l.

5. A buffer solution as claimed in claim 1 wherein said collagenase is present in a concentration of 3000 U/l.

* * * * *